US008092215B2

(12) United States Patent
Stone-Collonge et al.

(10) Patent No.: US 8,092,215 B2
(45) Date of Patent: Jan. 10, 2012

(54) SMILE DESIGNER

(75) Inventors: Michelle Stone-Collonge, Campbell, CA (US); Eric E. Kuo, Foster City, CA (US); Rick Matty, Scotts Valley, CA (US); Fabio Pettinati, San Jose, CA (US); Thomas Maurer, Santa Clara, CA (US); Dzmitry Sanko, Fremont, CA (US)

(73) Assignee: Align Technology, Inc., San Jose, CA (US)

( * ) Notice: Subject to any disclaimer, the term of this patent is extended or adjusted under 35 U.S.C. 154(b) by 456 days.

(21) Appl. No.: 12/154,634

(22) Filed: May 23, 2008

(65) Prior Publication Data

US 2009/0291408 A1 Nov. 26, 2009

(51) Int. Cl.
*A61C 3/00* (2006.01)
(52) U.S. Cl. .......................................... 433/24
(58) Field of Classification Search .................. 433/5–7, 433/18–24, 202.1, 218, 215; 703/2, 6; 700/118–119, 181; 705/2, 3
See application file for complete search history.

(56) References Cited

U.S. PATENT DOCUMENTS

2005/0089822 A1* 4/2005 Geng ............................ 433/215
2005/0271996 A1* 12/2005 Sporbert et al. ................ 433/24
2006/0154207 A1* 7/2006 Kuo ............................ 433/202.1

FOREIGN PATENT DOCUMENTS

WO WO 2007/019709 A2 2/2007
WO WO 2007/019709 A3 2/2007

OTHER PUBLICATIONS

Patterson Dental.*
Dentrix, "Dentrix G3, New Features". http://www.dentrix.com/g3/new_features/index.asp, accessed Jun. 6, 2008 (2 pgs).
Geomagic, "Dental Reconstruction". http://geomagic.com/en/solutions/industry/dental_desc.php, accessed Jun. 6, 2008 (1 pg).
Patterson Dental, "Cosmetic Imaging". http://patterson.eaglesoft.net/cnt_di_cosimg.html, accessed Jun. 6, 2008 (2 pgs).
Smart Technology, "Smile Library II". http://smart-technology.net/, accessed Jun. 6, 2008, (1 pg).
Smile-Vision, "The Smile-Vision Cosmetic Imaging System". http://www.smile-vision.net/cos_imaging.php, accessed Jun. 6, 2008 (2 pgs).
Yaltara Software, "Visual Planner". http://yaltara.com/vp/, accessed Jun. 6, 2008 (1 pg).
Methot, Alain. "Get the Picture . . . With a GPS for Smile Design in 3 Steps". Spectrum, vol. 5, No. 4. pp. 100-105.
"Get a Realistic Smile Simulation in 4 Steps with GPS, a smile management software". http://www.gpsdentaire.com/en/preview/ May 23, 2008.

* cited by examiner

*Primary Examiner* — Corrine M McDermott
*Assistant Examiner* — Yogesh Patel
(74) *Attorney, Agent, or Firm* — Brooks, Cameron + Huebsch, PLLC

(57) ABSTRACT

A method for designing a restored smile includes receiving scan data of a patient's teeth, developing a digital model of the patient's teeth via a computing device, where the model represents the patient's teeth based upon the scan data, creating a dental treatment plan to restore one or more teeth from an initial condition to a successive condition, and wherein a final condition of the one or more is based on the one or more teeth having at least one planned additional restorative tooth structure provided therewith.

12 Claims, 9 Drawing Sheets

SMILE DESIGNER

BACKGROUND

The present disclosure is related generally to the field of dental treatment. More particularly, the present disclosure is related to a method for designing and implementing a restored smile to improve the visual appearance of a patient's smile and in presenting a modified image of the patient showing the patient with the improved smile.

Treatments having to do with smile improvement can range from inexpensive to expensive and can range from generally non-invasive and/or time consuming to invasive and/or time consuming. For example, treatments can include whitening, reshaping and restoring, straightening or other movement of teeth, oral surgery (e.g., to remove teeth or bone mass), plastic surgery (e.g., cheeks, lips, other facial shaping, etc.), and other treatment types.

As the cost, invasiveness, and/or time period for treatment increases, the reluctance of a patient to go forward with the treatment may also increase, in some instances. It may also be difficult for some patients to understand what the end result of a treatment may be or how the overall effect on their appearance may be improved, which may also be a factor in deciding whether or not to move forward with a particular treatment.

Further, in dentistry one goal is often to conserve healthy tooth mass. However, in some instances, such as in some cosmetic dentistry procedures, healthy tooth mass may be removed aggressively to more quickly improve the smile of the patient. The removal of such healthy tooth mass may, in some instances, reduce the overall health and/or longevity of a patient's teeth.

Also, some treatment professionals may not have the level of skill or experience needed to properly design and implement an improved smile for a patient. Such treatment professionals may not be able to properly design a smile for a patient and therefore may create unhappy patients and can damage teeth requiring further corrective dental action, which can be costly and/or harmful to the teeth.

Additionally, within the dental profession, some treatment professionals may not have the skills, training, and/or resources to provide a comprehensive diagnosis and analysis of a patient's smile and/or the options to set the right patient expectations with respect to the plan to restore the smile. In such instances, patients may become unhappy when treatment professionals do not have the ability to provide proper smile restoration when completed.

DETAILED DESCRIPTION

Figure 1:
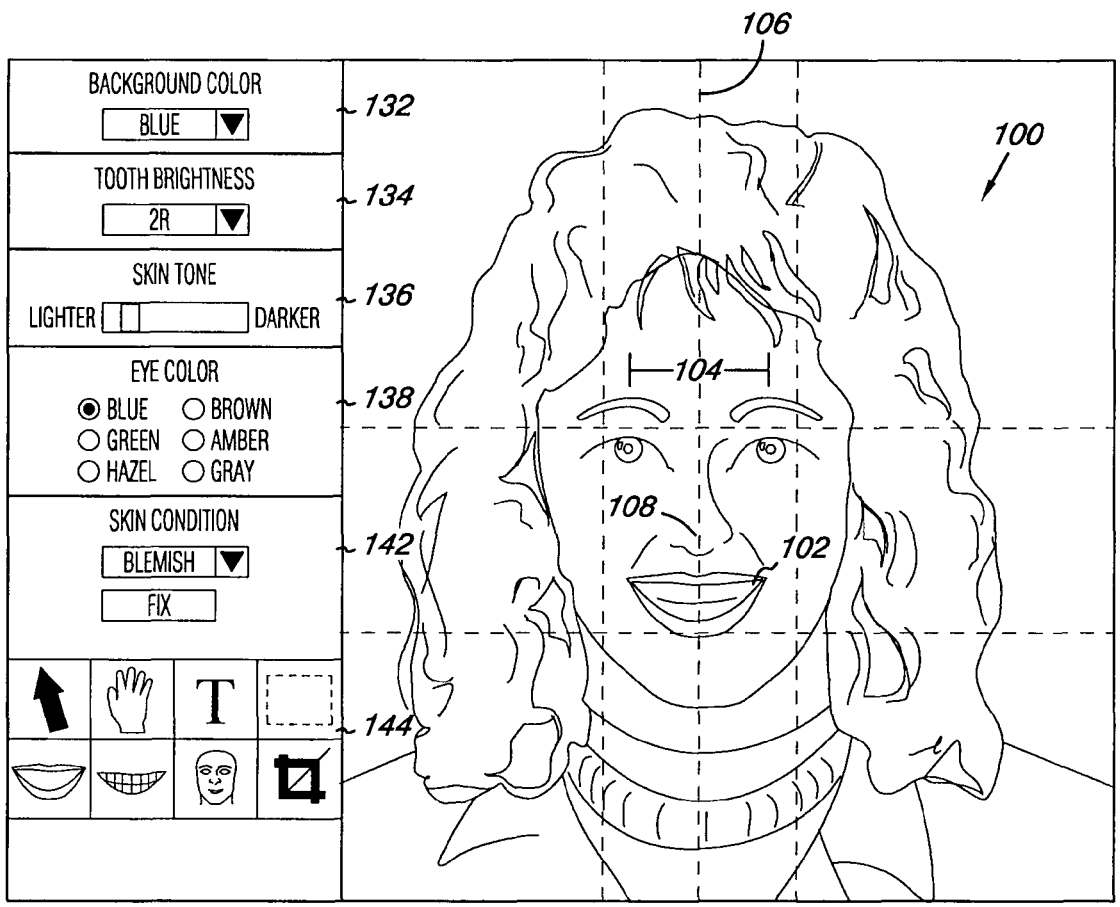
FIG. 1 illustrates an embodiment of a frontal image, on a user interface of a computing device, of a patient's face for designing a restored smile according to the present disclosure.

Embodiments of the present disclosure provide various methods and systems for designing and presenting a restored or proposed changed smile. Various embodiments include receiving scan data of a patient's teeth, developing a digital model of the patient's teeth via a computing device, where the model represents the patient's teeth based upon the scan data, creating a dental treatment plan to restore one or more teeth from an initial condition to a successive condition, and wherein a final condition of the one or more is based on the one or more teeth having at least one planned additional restorative tooth structure provided therewith.

Embodiments of the present disclosure are described in relation to the accompanying drawings, which will at least assist in illustrating the various features of the various embodiments. In the Figures, the first digit of a reference number refers to the Figure in which it is used, while the remaining two digits of the reference number refer to the same or equivalent parts of embodiment(s) of the present disclosure used throughout the several figures of the drawing.

FIG. 1 illustrates an embodiment of a frontal image, on a user interface of a computing device, of a patient's face for designing a restored smile according to the present disclosure. In various embodiments, a method can include providing a frontal image 100 of a patient's face including a smile as illustrated in the embodiment of FIG. 1. In some embodiments the frontal image 100 can be used to design a restored or changed smile (hereinafter just generally referred to as a restored smile) for a patient.

In some embodiments, the patient can visit a treatment professional to receive a diagnosis and treatment plan to change the patient's smile to a desired restored smile. For example, a portion of the diagnosis can be done by uploading a frontal image 100 of the patient's face to a computing device.

In some embodiments, a digital model can be developed having, for example, a digital model of the teeth or, in some embodiments, one or more facial features of the patient in combination with the digital model of the patient's teeth. Such embodiments can, for example, aid in the image being more realistic thereby allowing the potential patient an opportunity to more readily see the changes in context with their facial features, among other potential benefits.

In some embodiments, portions of the dental treatment plan can be illustrated by images showing what the smile would look like at one or more different stages of the plan. For example, in some embodiments, the dental treatment plan can be created to also include modeling a restorative tooth structure stage of the plan (e.g., after placement of one or more veneers).

In this manner, the prospective patient can see how he/she may look once that stage of the treatment has been accomplished. Such embodiments can be helpful, for example, in side-by-side comparison of before and after images, and/or for showing a progression from one stage to the next of from a first stage to a last stage among other comparisons and potential benefits.

In some embodiments, the image 100 can, for instance, be manipulated in the computing device by rotating, cropping, and/or adjusting the brightness, tone, and/or contrast of the photograph, among other techniques to allow the treatment professional a better view of the patient's smile to develop a treatment plan to implement a desired restored smile.

In some embodiments, the image 100 can, for example, be manipulated to manually or automatically detect and reduce glare and/or highlights caused by oily skin or another condition. This can be accomplished in any suitable manner. For example, executable instructions can be provide to a computing device that can manipulate the image (a device on which the image is displayed or on which a user has access to make a manipulation to an image displayed on another device).

In the embodiment illustrated in FIG. 1, a user interface presented on the computing device includes a space for viewing the patient including restored smile. In some embodiments, this space can be on a separate view than the editing tools shown in FIG. 1, and/or a split space can be provided to show the before restoration and after restoration, among other changes that could be made to the presentation of the information shown in the embodiment of FIG. 1.

In the embodiment of FIG. 1, the user interface includes a number of editing tools. More, less, or different tools may be provided in various embodiments and embodiments may allow tools to be added or removed from via user selection of tools to be available to them.

In the embodiment of FIG. 1, the editing tools include a background color tool 132, a tooth brightness tool 134, a skin tone tool 136, an eye color tool 138, a skin condition tool 142, and a number of other tools 144. These functionalities will be discussed in more detail below.

With respect to the skin condition editing functionality of FIG. 1, executable instructions can be used to, for instance, identify certain areas on an image that understood to become oily or contain another undesirable feature and can include instructions to analyze the data used to form the image to identify those areas that have a color or pattern that would indicate such an area (e.g., an oily or dry area). This data can then be adjusted based upon one or more patterns and/or colors that are present near the area or from another source such as a database of skin tone information (e.g., within the computing device or on another device), to reduce the glare or other such condition.

In some embodiments, such functionality can be done manually by a user of the computing device, automatically through executable instructions, and/or a combination of these. For example, the select area tool (i.e., the dashed box icon and button) in the other tools area 144 of the tool editor portion of the user interface can be used to select a portion of the image 100 to be analyzed for oily/dry skin or other skin conditions, or other uses provided in the editing area of the user interface.

In some embodiments, the teeth of the digital model can be manually adjusted. For example, if special tooth shapes are desired (e.g., extra pointy canines or extra flat canines, among others) the user of the computing device can make such adjustments. Such features can be accomplished using a tool from the user interface, similar to the other tool selections described herein.

Further, in some embodiments, some teeth shapes may be preselected to allow the user to more easily locate a desired or common tooth shape. Such tooth shapes can be stored in a database.

In some embodiments, such a tool can include executable instructions to create gaps where teeth may have been pulled or repositioned to create the gap. Such instructions could, for example, use a number of colors to color the position in which a tooth, or a portion thereof, resides. In some embodiments, the instructions can be used to identify the size of a gap from the scan data and/or data with respect to moving teeth.

In some embodiments, since the user of the computing device may not be skilled in using an image modification program, the number of options that the user may have access to may be limited. For instance, in some embodiments, a user interface may present virtual buttons, tabs, or other suitable user actuation mechanisms to initiate a particular functionality.

For example, the interface may have a button for eye coloration (e.g., red-eye, colored contacts, etc.) modification, oily skin modification, image artifact modification, skin condition modification (e.g., rash, discoloration, acne, blemish, etc.), image background modification, and/or other such features. In some such embodiments, when a user actuates a button, a number of executable instructions can be initiated to carry out the particular function desired by the user.

For example, with respect to skin condition, the embodiment of FIG. 1 includes a skin condition editing tool 142. In the illustrated embodiment of FIG. 1, the tool 142 includes a pull down menu of skin conditions and a fix button for initiating executable instructions for manipulating the image to reduce or remove the skin condition from the image. In some embodiments, the selection of a skin condition from the pull down menu can change the instructions that are executed and, in turn, the result on the image.

For instance, if a blemish is selected on the pull down menu, the computing device will execute instructions for identifying a blemish (e.g., a scar, acne, canker sore, or other type of skin disruption) within the selected area of the image (e.g., using the image as a whole, a selection made using the select area tool, or one of the other tools provided) and will manipulate the image to reduce or remove the blemish from the image. If oily skin is selected, a different set of executable instructions may be utilized that will better manipulate the image in order to reduce or remove the oily skin look from the image.

In the embodiment of FIG. 1, the user interface provides a certain number of background colors, tooth brightness options, skin tones, lighting conditions, eye colors, and skin conditions. By limiting these in some manners, it may be helpful for the user in being able to effectively create an image that forecasts what the patient will look like when the treatment has finished or at a particular phase in treatment.

For instance, in some embodiments, the image 100 can be processed by having the background behind the patient's face replaced with a neutral color or pattern that may present the patient's face in a more attractive manner. For example, in some situations a light-colored individual may benefit from having a darker background and a dark-colored individual may benefit from a lighter background.

Such changes can be accomplished manually or automatically. In the embodiment of FIG. 1, the selection of background is accomplished through the selection of a color from a pull down menu. In the illustrated embodiment, the selection initiates the change in the background color. It is to be understood that other manners of presenting information with regard to color selection (or any other editing function) can be utilized and sever other mechanisms for presenting such information are illustrated herein (e.g., pull down menus, sliding scale selectors, selection bubbles, buttons, etc.)

In various embodiments, the data for the entire image can be analyzed and, in some embodiments, an area within the image can be defined for analysis. Selection of an area can, for example, be accomplished manually or by executable instructions. For example, as discussed above, a select area tool (i.e., the dashed box icon and button) in the other tools area 144 of the tool editor portion of the user interface can be used to select a portion of the image 100 to be analyzed for oily/dry skin or other skin conditions, or other uses provided in the editing area of the user interface.

In some embodiments, the number of choices can be limited so that the user may have an easier time manipulating the image or portion thereof. For example, if the teeth are selected for manipulation, the color palette could be adjusted/limited so that only reasonable tooth colors would be available (e.g., different shades of white and/or off-white as opposed to green, purple, red, etc). For instance, in the embodiment of FIG. 1, a pull down menu 134 is provided that includes brightness levels taken from the Vita scale of tooth whiteness. Other such scales or color ranges can be used in the various embodiments disclosed herein.

Such a feature may allow a user that is not particularly experienced to select a proper and/or suitable color. Such an embodiment may also make the selection process quicker so that the user can manipulate the image and show it to a patient within a shorter timeframe.

In various embodiments, the treatment professional can identify key features of the image in the computing device, such as tooth shade 102, the interpupillary distance 104, the facial midline 106, and the dental midline 108, among other features. In some embodiments, these and/or other features can be used to design a smile that fits the patient's face and/or can be achievable through restorative procedures. In some embodiments, the treatment professional can adjust these key features to better reflect standards and norms related to patient's complexion, ethnicity, and age among various other factors.

With respect to the embodiment of FIG. 1, the editing area of the user interface includes a skin tone editing tool 136. This can be used to adjust the color of the patient's skin (via a sliding scale selector) to make it more realistic with respect to their actual skin color or to add or remove skin color if a patient is abnormally light skinned or over tanned, among other issues. The embodiment of FIG. 1 includes a face button in the other editing tools area 144 of the user interface which can be used to select the face of the patient's image in order to make changes thereto.

The select area tool discussed above can be similarly used to make changes as described herein to the face of the patient's image. In some embodiments, the select area tool may be able to capture different area shapes. For example, the area illustrated in FIG. 1 is a rectangle (e.g., the rectangular dashed box), but circles, oval, squares, irregular shapes, shapes defined by the user (e.g., by selecting points on the images to defined an area) can be suitable mechanisms for providing such functionality.

In various embodiments, executable instructions can be executed by a computing device to identify the location of the lips, and/or smile. This can be accomplished in any suitable manner. Such embodiments can, for example, identify the color range of the lips versus other colors on the image (e.g., cheeks, nose, teeth, gums, etc.) based on the color data of such portions of the image.

Another technique could be to lighten the image until only the lips are still shaded, since the lips are the darkest facial feature in some instances. The image could similarly be darkened until only the teeth are featured since the teeth are the lightest facial feature in some instances. As indicated above, other suitable methods may be utilized and such methods can be accomplished through use of instructions executed by a computing device.

In the embodiment of FIG. 1, the user interface includes a lips button in the bottom left corner of the other tools area 144. In some such embodiments, by selecting this feature, instructions can be initiated and executed to select the lips as described above and then changes the look of the lips can be made or the lip lines can be adjusted for other purposes, as described herein.

The embodiment of FIG. 1 also includes a teeth button in the other editing tools area 144 of the user interface. This can similarly be used to select the teeth of the patient's image for adjustment.

Figure 2:
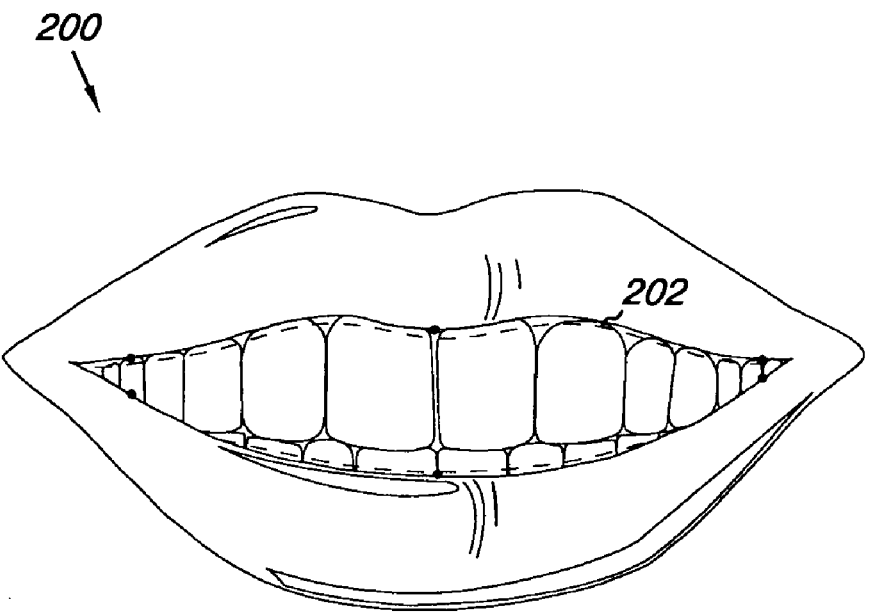
FIG. 2 illustrates an embodiment of a patient's smile for designing a restored smile according to the present disclosure.

FIG. 2 illustrates an embodiment of a patient's smile for designing a restored smile according to the present disclosure. In various embodiments, the frontal image can be provided in a digital format to a computing device illustrated in FIG. 1 and can be cropped to show the patient's smile 200, as illustrated in FIG. 2. In some embodiments, the computing device can automatically crop and/or scale image 100 to create patient's smile 200.

In some embodiments, the computing device can include executable instructions that are executable to identify the patient's inner lip line 202. This can, for example, be accomplished by mapping a number of reference points on the image and then creating a line that intersects the points. In some embodiments, the treatment professional may not have to precisely identify these reference points, but rather, executable instructions can be used to automatically adjust the position of the reference points to the actual inner lip line 202, for example, through use of techniques described herein with regard to identifying the lips or teeth on the image.

The patient's inner lip line 202 can be used, for example, to identify the area in the patient's mouth where the patient's teeth are showing in the patient's smile, among other uses. In some embodiments, the patient's inner lip line 202 can indicate where changes to the patient's occlusion may affect the appearance of the patient's smile.

In various embodiments, the patient's inner lip line can be edited. This can be accomplished, for example, by providing executable instructions to move the line or one or more points that are used to form the line. This movement can be accomplished by input from a user through a user interface, for example. In some embodiments, the computing device can automatically adjust the patient's inner lip line by moving, adding, or removing points along the lip line.

The location of the patient's teeth in relation to the patient's lip can be modified to create a more desirable smile. In some embodiments, a computing device can include executable instructions to identify a number of teeth within the boundaries of the patient's inner lip line 202.

As used herein, the inner lip contour is the border line between the lips on the outside and the teeth, gum, and/or open mouth on the inside. The following provides a description of how the lip line can be identified automatically, semi-automatically, and/or manually.

In some embodiments, a number of initial points can be manually placed by a treatment professional. In various embodiments, these points can be identified using a computing device and a set of executable instructions through a manner as described herein or another suitable manner.

In the embodiment illustrated in FIG. 2, the inner lip line has six defined points. Embodiments of the present disclosure can use more or less points.

In some embodiments, as shown in FIG. 2, four points are provided in the corners of the mouth. This can be beneficial, for example, so that no open mouth area or teeth may be left on the outside of the created lip line. Some embodiments, also as illustrated in FIG. 2 provide a point on both the upper and lower portions of the lip line.

It may be beneficial in some embodiments, to place the one or both of the point close to the center of the mouth. This can be beneficial, for example, to identify the symmetrical or non-symmetrical aspects of the smile.

In some embodiments, executable instructions can be utilized to automatically extract the edges of the lips forming the lip line. For example, this can be accomplished by using luminance (brightness) and chrominance (color) information. In such embodiments, the vertical gradient can, for example, be computed to extract the horizontal edges in the mouth image.

In various embodiments, a computation can be done for the upper and lower lips. In some such embodiments, a result can be an edge image that contains both the inner lip contour and other edges, such as teeth and/or gums. In addition, a highlight removal algorithm can be applied, in some embodiments, before the edge extraction, to reduce the creation of false edges, if needed.

In some embodiment, the points initially placed can be automatically connected through use of executable instructions. For example, in some embodiments, the computation for the upper and lower lip can be done independently for each lip.

In such embodiments, and for reference, using the points illustrated in FIG. 2 as an example, for each lip, the three initial points are connected by an initial fit (e.g., straight lines or parabola), points can then be distributed along this line in small intervals. A cost function can be used minimized which can, for example, include: strength of an edge at the position of the points, distance from the six initial points, curvature of the line, and deviation of the point interval length from a mean.

Points can then be iterated through and moved while minimizing the cost. When the cost does not decrease any more, the process has converged. In some embodiments, the cost function can, for example, be computed on a down sampled image first and then can be refined at original size.

In some embodiments, a treatment professional can manually correct individual points as needed via a user interface and executable instructions. In such embodiments, the treatment professional can check the output and can move points, for example, through use of a mouse, if necessary to adjust the segmentation to the preference of the treatment professional.

Figure 3:
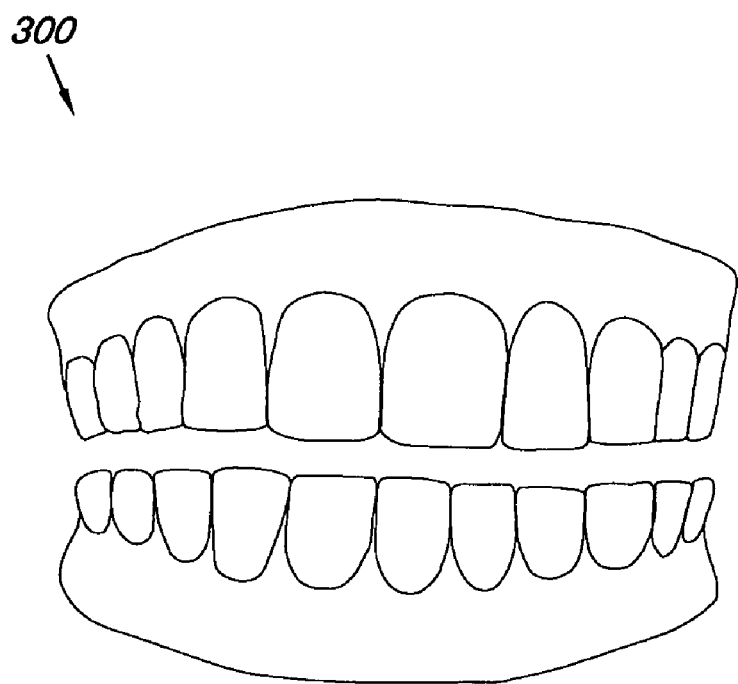
FIG. 3 illustrates an embodiment of an image of a patient's teeth for designing a restored smile according to the present disclosure.

FIG. 3 illustrates an embodiment of an image of a patient's teeth for designing a restored smile according to the present disclosure. In the embodiment illustrated in FIG. 3, the patient's teeth are photographed and/or scanned to allow a treatment professional to analyze the dental condition of the patient.

The image that is created of the patient's teeth can allow the treatment professional to determine a dental treatment that can provide at least a portion of the necessary improvements for a restored smile. The patient's teeth can be moved through dental treatment to improve the patient's occlusion and at least partially restore the patient's smile.

In the embodiment shown in FIG. 3, the image 300 of the patient's teeth is shown to aid in the treatment professional's diagnosis of the patient's dental condition. In some embodiments, a number of images are taken of the patient's teeth from a number of angles and perspectives. These images can be used in combination with an impression of the patient's teeth and/or a digital model of the patient's teeth to determine the dental treatment that will help the patient achieve a restored smile.

Figure 4:
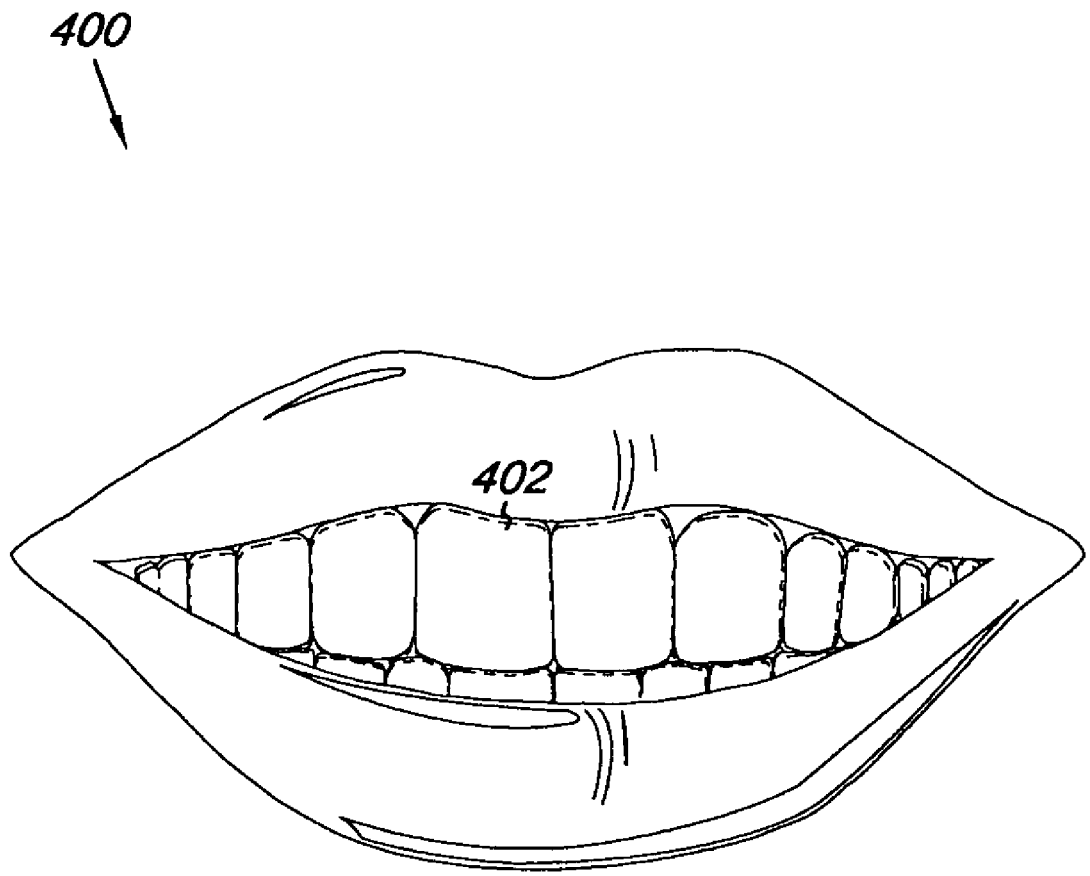
FIG. 4 illustrates an embodiment of an image of a patient's smile with a restored smile superimposed over the patient's smile according to the present disclosure.

FIG. 4 illustrates an embodiment of an image of a patient's smile with a restored smile superimposed over the patient's smile according to the present disclosure. In the embodiment illustrated in FIG. 4, the patient's smile 400 has a potential restored smile 402 superimposed over the patient's smile 400.

This is done to allow the patient and/or treatment professional to visualize the appearance of the restored smile after treatment. The restored smile may be of all the displayed teeth or may be of any number including at least one tooth in the smile.

In various embodiments, the treatment professional can superimpose a number of restored smiles from a smile library database of potential restored smiles to determine the restored smile that is the most appealing to the patient. This can allow the patient to visually see how different smiles would look with their face and/or in their mouth. In some embodiments, a computing device can include executable instructions to guide the treatment professional in placing the restored smile in accordance with established esthetic principles.

The patient can select a smile configuration that is desirable based upon the smiles viewed from the smile library database. Additionally, a treatment professional and/or computing device executable instructions can be used to aid in the selection of one or more smiles from the library that may better fit the patient's mouth. This may be accomplished, for example, by looking at the number of teeth, position of teeth, position of gingiva, size of oral cavity, bone structure, and/or other factors.

In various embodiments, the method of designing a restored smile allows the treatment professional to enter patient information, upload a frontal image, edit and/or optimize the frontal image, and/or identify key patient landmarks and/or measurements. The treatment professional can use a computer readable program executable on a computing device to select a dentition similar to the patient which will be used to show the value of the overall treatment plan.

Using an included smile library, the treatment professional can swap out smiles on the patient's image to illustrate various looks. In some embodiments, these smiles can be visible on both the patient's images, as well as the treatment plan that is developed to implement the restored smile.

In some embodiments, executable instructions can be utilized such that the doctor may be able to toggle between the actual smile and the proposed smile or make one or the other semi-transparent so as to view a superimposed image of the two to observe the differences in position, shape, and size, for example. In some embodiments, the database can include common smile configurations, popular smile configurations, selected by previous prospective patients, and/or specialized smile configurations, like those of celebrities, among other types of smiles.

Figure 5:
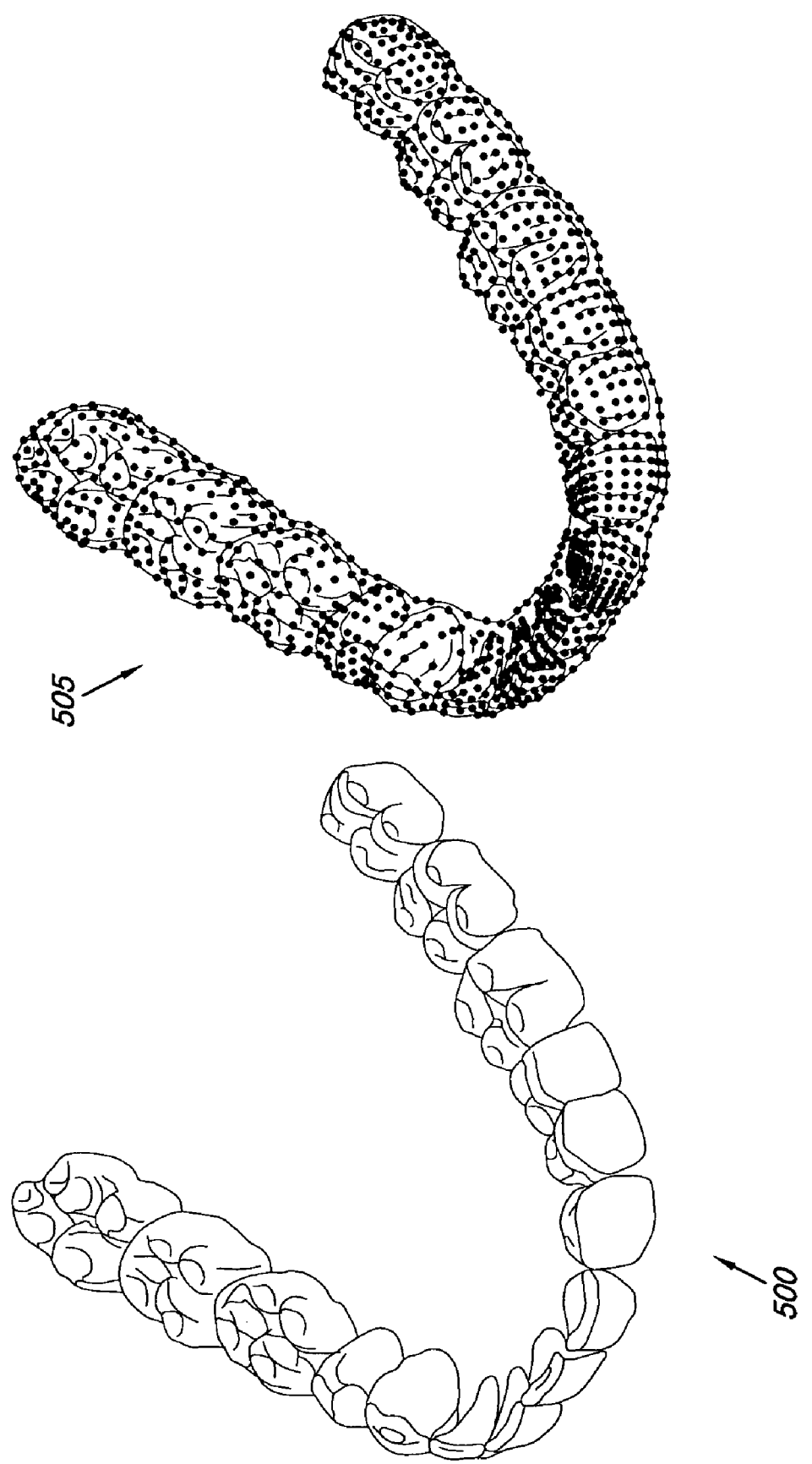
FIG. 5 illustrates an embodiment of an impression of a set of teeth and a digital model of the set of teeth according to the present disclosure.

FIG. 5 illustrates an embodiment of an impression of a set of teeth and a digital model of the set of teeth according to the present disclosure. In various embodiments, the impression of the user's teeth 500 can be taken with an impression kit.

The impression of the user's teeth 500 or the teeth of the patient can then be scanned and the data gathered by the scan can then be used to form a digital model of the impression of user's teeth 505. The digital model of the impression of the user's teeth 505 can, for example, provide a digital image of the user's teeth that maps the outside surface (e.g., using a number of points) of the impression of the user's teeth 500 to allow 360° viewing the user's teeth. The digital model 505 can then be studied by a treatment professional to determine if a dental condition exists with the user's teeth, which can be easier and can be more thoroughly studied for longer time periods than looking into the mouth of the user while the user is at the treatment professional's office.

In various embodiments, the patient can select a restored smile that the patient wants to achieve through treatment and the treatment professional can analyze the patient's teeth with images and digital models of the patient's teeth, a treatment plan can be prescribed by the treatment professional. The treatment plan can include a number of methods, including the moving of one or more teeth, movement and/or change to the gingiva, removal of bone mass, and/or addition or removal of tooth mass, among other methods.

In some embodiments, a treatment plan can be created based upon the comparison of the digital model of the user's teeth to the existing cases indexing database. Various prior treatment plans of prior patients can be stored in the existing cases indexing database.

In such embodiments, the treatment plan can be derived from the treatment plans of prior patients by comparing dental conditions to their response to various treatment plans. Prior treatment plans that were used to treat to dental conditions that are similar to the user's dental condition can, for example, be identified and used as part of the treatment plan that is generated during the comparison of the digital model to prior cases in the automated evaluation process.

In various embodiments, the treatment plan can be implemented by the treatment professional when the patient commits to moving forward with the treatment plan. In some embodiments, the treatment professional can submit patient records to a computing device for automated analysis, receive an automated analysis for the patient that details the patient's orthodontic treatment, as well as illustrates the final restorations and/or what the smile will look like on the three-dimensional teeth in the mouth, and/or on the face of patient.

In some embodiments, the treatment plan can include an analysis of the current occlusion and the benefits that orthodontia will play in the outcome, such as tooth depth and/or mass reduction, root canal risk, etc. In some embodiments, the final smile can be visible in a number of views such as the patient frontal and smile close-up image views, among others.

In various embodiments, the treatment professional can have the ability via the smile database to make incremental changes to the smile to make sure the patient has the smile that they want before accepting the proposed treatment. This can be accomplished, for example, by utilizing executable instructions for movement of one or more teeth, movement and/or change to the gingiva such as gingival contouring from crown lengthening, removal of bone mass, and/or removal of tooth mass, among other methods. In some embodiments, the process of making incremental changes to the smile can be an iterative process between the treatment professional and a computer executable program on a computing device that can design restored smiles, as the process can include modifications to the dental setup and/or the three-dimensional final restoration.

In some embodiments, after designing the smile for the patient and accepting the treatment plan, the treatment professional can receive a physical model of the final restoration, and a template aligner of this restoration to be used when creating a provisional final restorative model for the patient.

In some embodiments, the final position model and template can be sent to the treatment professional. The treatment professional can also receive aligners that can be used to implement the dental treatment portion of the treatment plan. The aligners can be sent to the treatment professional and used in a similar manner as aligners that are sent for only an orthodontic treatment.

In various embodiments, once an orthodontic treatment portion of the treatment plan is completed, the treatment professional can have the ability to create a comprehensive treatment form for submission to a lab of their choice for ceramic veneer manufacturing. In some embodiments, the form can be pre-populated with existing information regarding the patient's dental condition and/or provide guided questions and/or free-form data entry.

In various embodiments, once the orthodontic portion of the treatment plan is complete, the treatment professional can begin cosmetic restorations. In some such embodiments, the treatment professional can, for example, remove tooth mass using a template as a guide. The treatment professional can remove tooth mass until a template fits in the patient's mouth, for example, with enough depth for ceramic veneers. In such embodiments, the treatment professional can then take an impression of the patient's teeth.

In some embodiments, the treatment professional can fill the template with resin and insert it in the patient's mouth. The resin can cure on the patient's teeth and the template can be removed from the patient's mouth. In various embodiments, final adjustment can be made to the patient's smile by adjusting the resin on the patient's tooth.

In various embodiments, an impression of the patient's teeth with the resin on them can be taken by the treatment professional. The impression of the patient's teeth with the resin and the impression of the patient's teeth without the resin can, for example, be used to create a set of ceramic veneers. Resin veneers can, for example, be used as provisional restorations, or also as permanent restorations (if ceramic veneers are not subsequently created), or with additional adjustments such as heat curing or shade modification. If ceramic veneers are created, such veneers can be bonded to the patient's teeth and the patient has their desired restored smile.

Figure 6:
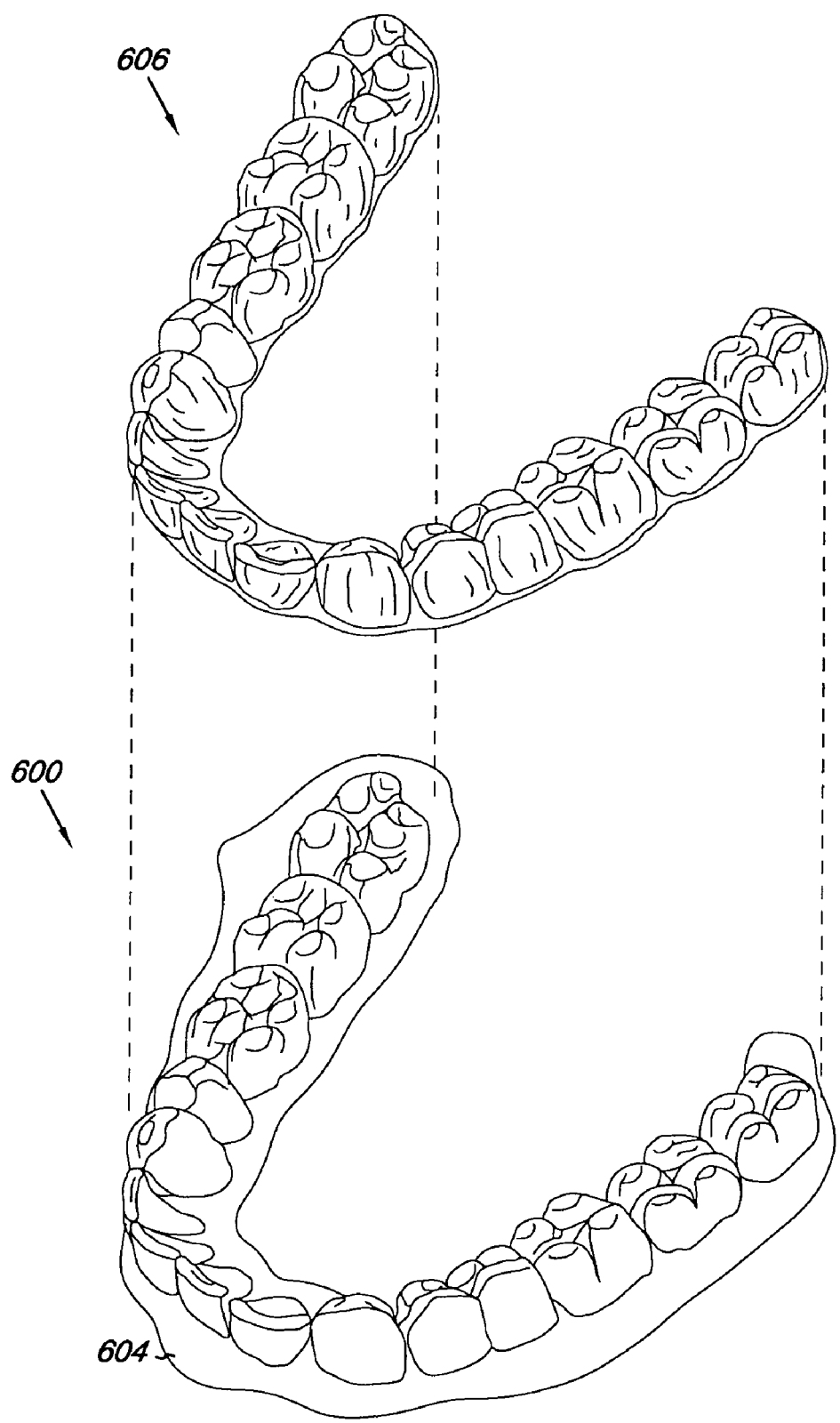
FIG. 6 illustrates an embodiment of the patient's teeth and an orthodontic appliance to treat a dental condition of the patient according to the present disclosure.

FIG. 6 illustrates an embodiment of the patient's teeth and a dental appliance to treat a dental condition of the patient according to the present disclosure. In the embodiment illustrated in FIG. 6, the patient's teeth 600 are treated with an aligner 606 to move the patient's teeth according the treatment plan. The aligner 606 can be placed over the patient's teeth 600 onto the patient's gingiva 604. The aligner 606 can move the patient's teeth 600 by applying pressure to the teeth. In some embodiments, several aligners can be used to incrementally move the patient's teeth into the desired position to improve the patient's occlusion.

In various embodiments, a number of dental appliances can be given to the patient to implement the dental treatment to the patient's teeth that is part of the treatment plan. Each of the appliances can be used in succession to incrementally move the patient's teeth. In some embodiments, each aligner can be used by the patients for varying amounts of time depending on the distance each aligner moves the patient's teeth. One aligner can be used for 1-3 weeks, for example, among other time periods.

Figure 7:
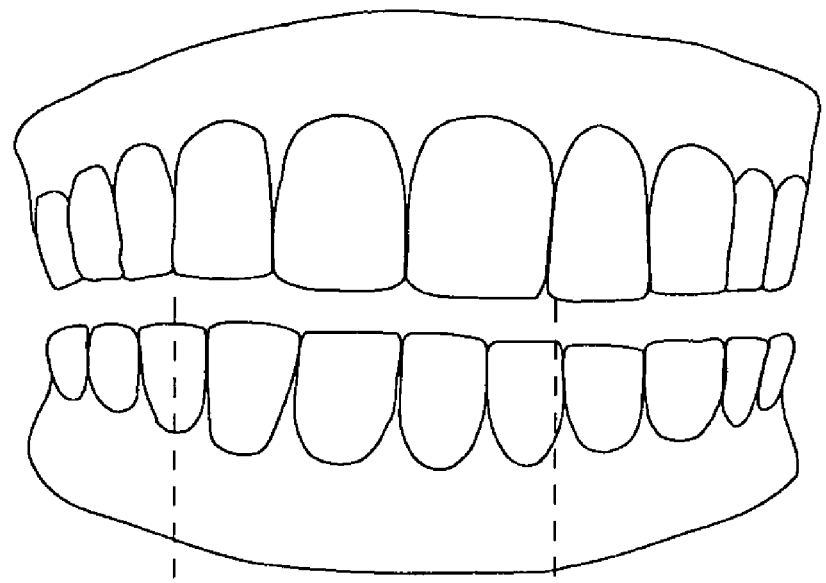
FIG. 7 illustrates an embodiment of the patient's teeth after the teeth have been treated for a dental condition and are prepared for an additional restorative tooth structure according to the present disclosure.

FIG. 7 illustrates an embodiment of the patient's teeth after the teeth have been treated for a dental condition and are prepared for an additional restorative tooth structure according to the present disclosure. In the embodiment of FIG. 7, the patient's teeth 700 have been treated to improve the patient's occlusion. The improved occlusion can be part of the treatment plan to restore the patient's smile.

In some embodiments, the patient's teeth can have a portion of the tooth removed to allow the patient's teeth to be prepared for the addition of a restorative tooth structure. The treatment professional can remove tooth mass using a template as a guide.

In some embodiments, an aligner may serve as the template. In some embodiments, the template can be created as part of a treatment plan to allow the treatment professional to only remove the portion of the patient's teeth for the restored smile and not to damage the patient's teeth with excessive tooth mass removal or excessive depth in the preparation(s).

The treatment professional can remove tooth mass until a template fits in the patient's mouth with the correct amount of depth for ceramic veneers, for example. The treatment professional can then take an impression of the patient's teeth.

Figure 8:
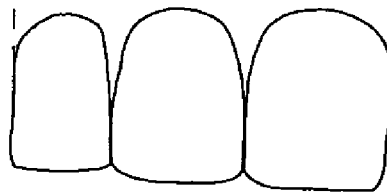
FIG. 8 illustrates an embodiment of an additional restorative tooth structure according to the present disclosure.

FIG. 8 illustrates an embodiment of an additional restorative tooth structure according to the present disclosure. In the embodiment of FIG. 8, the restorative tooth structure 800, can be placed over the patient's teeth that have had tooth mass removed and bonded to the patient's teeth to provide the restored smile for the patient.

In various embodiments, the restorative tooth structure can include a dental veneer template. The dental veneer template can, for example, be scaled to the dimensions of the patient's teeth incorporated into the treatment plan. In some embodiments, the color, contour, and/or relative tooth size of the dental veneer template can be modified.

In some embodiments, the restorative tooth structure 800 can be fabricated through an impression molding process. In some embodiments, the treatment professional can fill the template with resin and insert it in the patient's mouth. The resin can cure on the patient's teeth and the template can be removed from the patient's mouth. In various embodiments, final adjustment can be made to the patient's smile by adjusting the resin on the patient's tooth.

In various embodiments, an impression of the patient's teeth with the resin on them can be taken by the treatment professional. The impression of the patient's teeth with the resin and the impression of the patient's teeth without the resin can be used to create a set of veneers, among other functions. In some embodiments, the veneers can be bonded to the patient's teeth to form the occlusion for the patient's restored smile.

Figure 9:
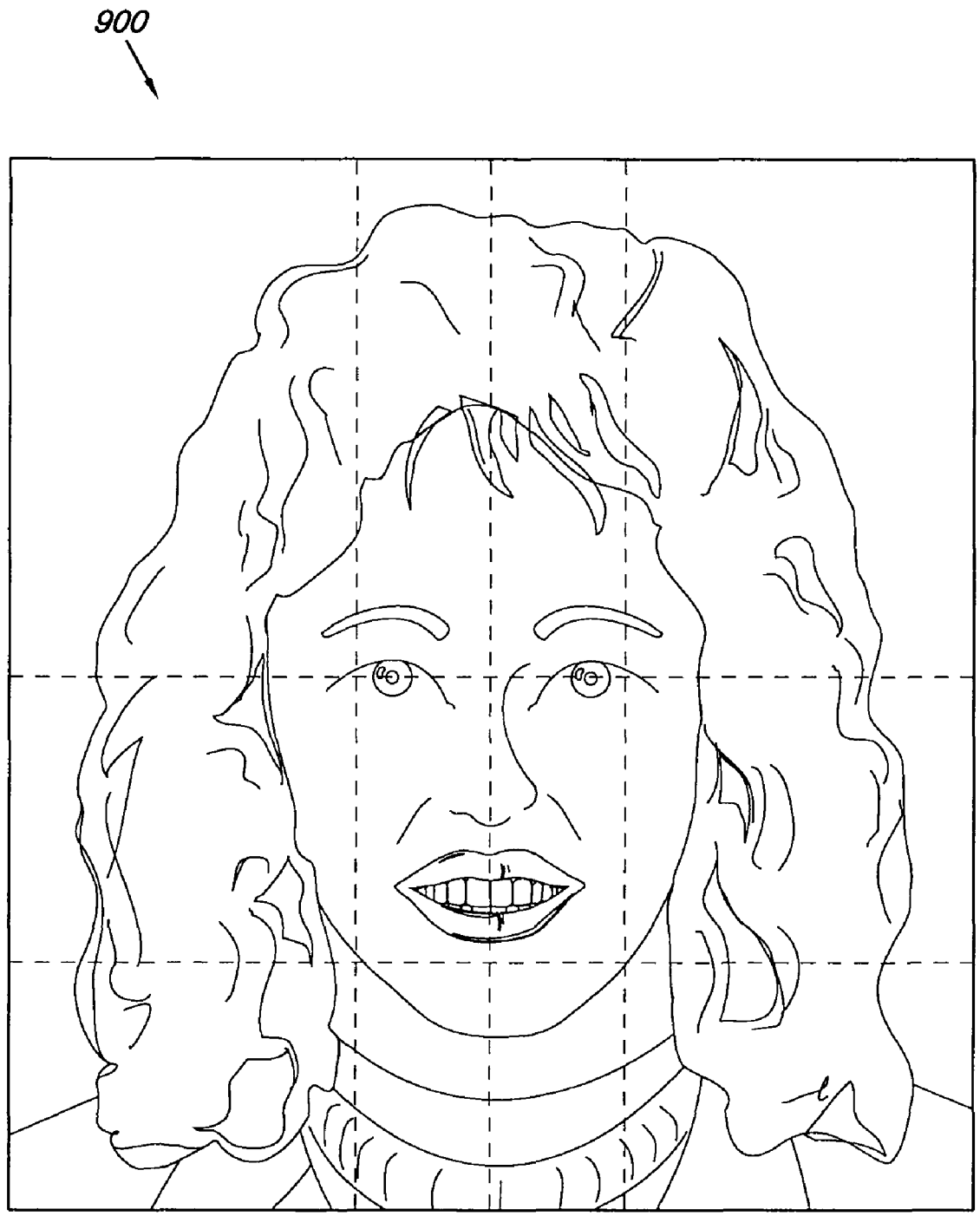
FIG. 9 illustrates an embodiment of a frontal photograph of a patient's face after treating a dental condition and adding a restorative tooth structure according to the present disclosure.

FIG. 9 illustrates an embodiment of a frontal image of a patient's face after treating a dental condition and adding a restorative tooth structure according to the present disclosure. In the embodiment of FIG. 9, the frontal image 900 of the patient's face illustrates the restored smile of the patient after implementation of the treatment plan. The frontal image 900 can be used to illustrate the effects of the treatment plan in achieving the restored smile to the patient, among other uses.

In various embodiments, the frontal image can also be stored in a database to show other patient's the restored smile results of a treatment plan. The image can be used by other patient's to select a restored smile that would be desirable, for example. In some embodiments, other patient's can superimpose the restored smile over an image of their face to visualize the restored smile on their face.

Figure 10:
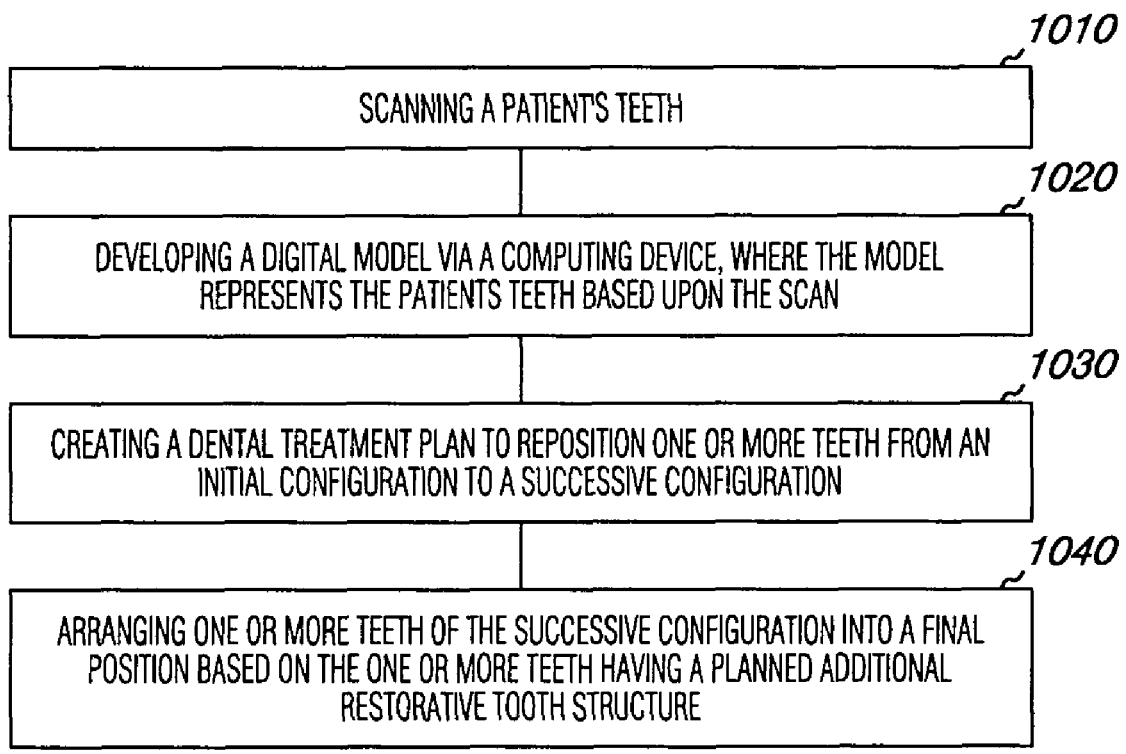
FIG. 10 illustrates a method embodiment for treating a dental condition and adding a restorative tooth structure according to the present disclosure.

FIG. 10 illustrates a method embodiment for treating a dental condition and adding a restorative tooth structure according to the present disclosure. The embodiment of FIG. 10 includes scanning a patient's teeth 1010.

The embodiment of FIG. 10 also includes developing a digital model via a computing device, where the model represents the patient's teeth based upon the scan 1020 and creating a dental treatment plan to reposition one or more teeth from an initial configuration to a successive configuration 1030. In the embodiment of FIG. 10, the method includes arranging one or more teeth of the successive configuration into a final position based on the one or more teeth having a planned additional restorative tooth structure 1040.

Figure 11:
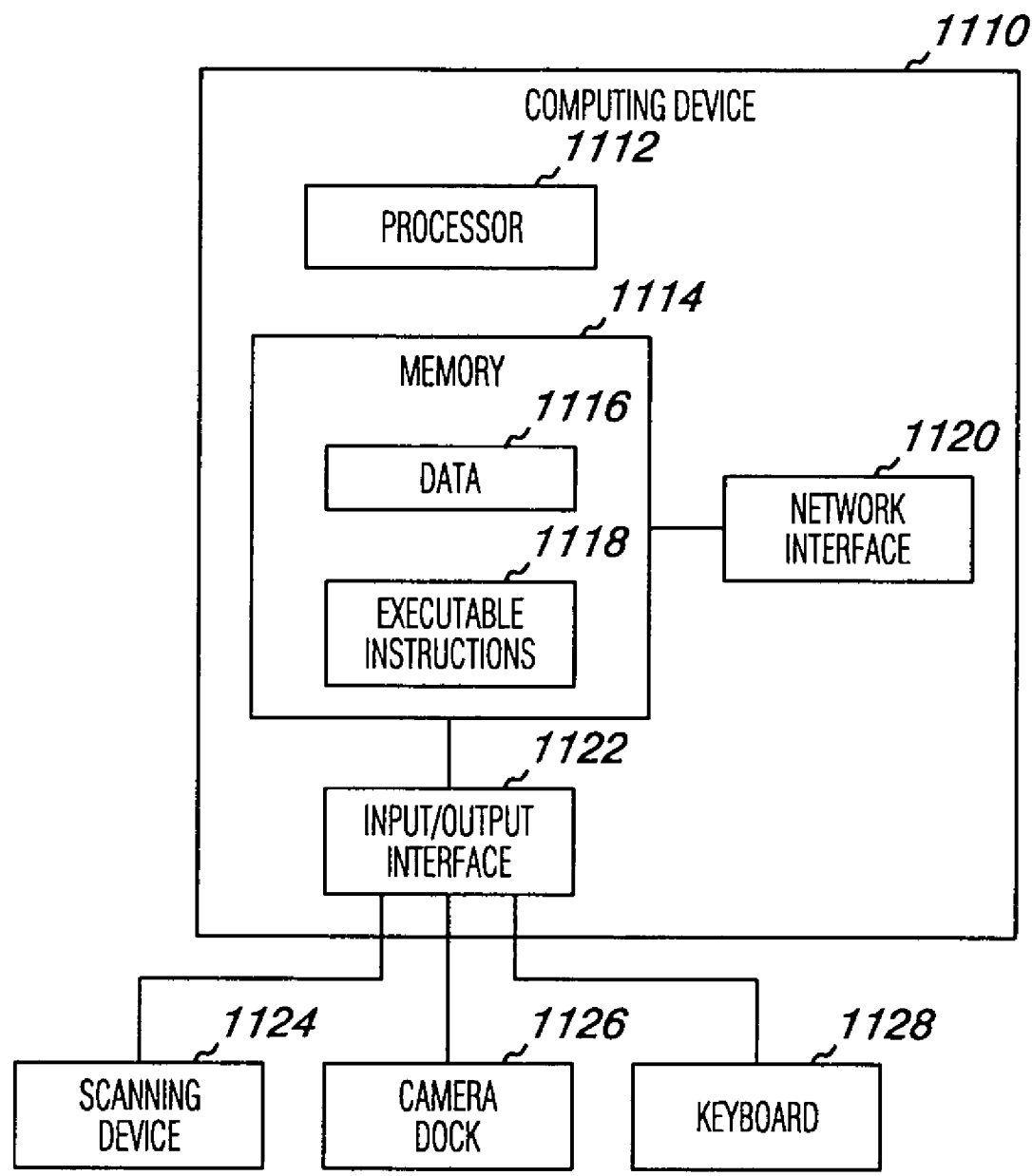
FIG. 11 illustrates an embodiment of a computing device to perform a method embodiment for treating a dental condition and adding a restorative tooth structure according to the present disclosure.

FIG. 11 illustrates an embodiment of a computing device to perform a method embodiment for treating a dental condition and adding a restorative tooth structure according to the present disclosure. The computing device 1110 illustrated in FIG. 11, includes a processor 1112 and memory 1114. Memory 1114 can include various types of information including data 1116 and/or a number of computing device executable instructions 1118 as discussed herein.

Memory can be used for a variety of different functions in the various embodiments. For example, memory can be used to store executable instructions that can be used to interact with the other components of the network including other computing devices and/or can be used to store information, such as instructions for manipulating one or more files.

For instance, in some embodiments, a computing device can include executable instructions for saving a number of scans and/or digital models to one or more files in memory. Such instructions can, for example, be instructions for saving local scans and/or digital models, scans and/or digital models from another computing device on a network, or a combination of two or more of these.

Additionally, as illustrated in the embodiment of FIG. 11, a system can include a network interface 1120. Such an interface can allow for processing on one or more networked computing devices or such devices can be used to transmit and/or receive scans and/or digital models and/or executable instructions for use with various embodiments provided herein.

The network interface 1120 can connect the computing device to a network. The network can be connected to other computing devices that can execute scans and/or digital models of the user's teeth.

A digital model obtained from a scanner that is interfaced with computing device 1110 can be sent on the network to other computing devices. A number of treatment professionals can have access to the computing devices on the network so they can view and diagnose the dental condition of a user based on the digital model from a remote location.

As illustrated in the embodiment of FIG. 11, a system can include one or more input and/or output interfaces 1122. Such interfaces can be used to connect the computing device with one or more input and/or output devices.

For example, in the embodiment illustrated in FIG. 11, the system includes connectivity to a scanning device 1 124, a camera dock 1126, and a keyboard 1128. The scanning device 1 124 can be used to scan the user's teeth.

The data from the scan of the user's teeth can be used to form a digital model of the user's teeth, which treatment professionals can use to diagnose a dental condition of the user's teeth, among other uses. The camera dock 1126 can receive a camera that can take images of the patient's face and teeth and the images can be uploaded to the computing device 1112.

Such connectivity on a network can allow for the input and/or output of manipulations (e.g., changes to the common file embedded in executable instructions) among other types of information. Although some embodiments may be distributed among various computing devices within one or more networks, such systems as illustrated in FIG. 11, can be beneficial in allowing for the capture, calculation, and/or analysis of the various information discussed herein.

Various embodiments include the use of executable instructions to accomplish one or more processes. Such instructions can, for example, be implemented on one or more computing devices and therefore in such embodiments, the executable instructions should be viewed as being computing device executable instructions for implementation by one or more computing devices.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A computing device implemented method for designing a restored smile, the method comprising:
   receiving scan data of a patient's teeth;
   developing a digital model of the patient's teeth via the computing device, where the model represents the patient's teeth based upon the scan data;
   receiving image data of a smile of the patient including at least a frontal image of a patient's lips defining the smile and teeth of the patient that are visible between the lips in the smile data;
   mapping a number of reference points in the image data of the smile and creating a line that intersects the reference points that defines an inner lip line of the smile;
   creating a dental treatment plan for the digital model of the patient's teeth to move one or more of the patient's teeth from an initial condition through a number of successive conditions to a final condition, wherein the final condition includes one or more teeth having at least one planned additional restorative tooth structure provided therewith;
   combining the digital model of the patient's teeth with the image data of the smile of the patient including the inner lip line of the smile; and
   showing the smile as it would appear in the final condition according to the inner lip line and the digital model in the final condition.

2. The method of claim 1, wherein the method includes developing a digital model of one or more facial features of the patient in combination with the digital model of the patient's teeth.

3. The method of claim 1, wherein the method includes creating the dental treatment plan to also including modeling a restorative tooth structure stage of the plan.

4. The method of claim 1, wherein the method includes editing the inner lip line of the smile in the model.

5. The method of claim 4, wherein the method includes identifying a number of teeth within a boundary area of the inner lip line of the smile.

6. The method of claim 5, wherein the method includes scaling a dental veneer template based on the identified teeth to dimensions of the patient's teeth.

7. The method of claim 5, wherein the method includes previewing a number of smile configurations from a smile library.

8. The method of claim 7, wherein the method includes selecting a smile configuration from the smile library.

9. The method of claim 8, wherein the planned additional restorative tooth structure is based on the selected smile configuration.

10. The method of claim 9, wherein the identified teeth are modeled in the dental treatment plan having the planned additional restorative tooth structure based on the selected smile configuration.

11. The method of claim 10, wherein the method includes designing a series of removable dental positioning appliances to implement the orthodontic treatment plan.

12. The method of claim 11, wherein the series of removable dental positioning appliances are fabricated to re-position the identified teeth with respect to a number of teeth not having the planned additional restorative tooth structure.

* * * * *